July 4. 1961 R. V. SCHREINER Plant Pat. 2,067

IRIS PLANT

Filed Sept. 27, 1960

WITNESS

Addison E. Avery

INVENTOR

ROBERT V. SCHREINER by: Rummler and Snow

ATTY.

United States Patent Office

Plant Pat. 2,067
Patented July 4, 1961

2,067
IRIS PLANT

Robert V. Schreiner, Rte. 2, Box 297, Salem, Oreg.
Filed Sept. 27, 1960, Ser. No. 58,866
1 Claim. (Cl. 47—60)

My present discovery relates to a new and distinct variety of Iris plant which was developed in my nursery in Salem, Oregon, from a cross of the variety "Opal Beauty" (unpatented) and the variety "Pathfinder" (unpatented).

The main result of this invention is the creation of a new Iris plant which possesses certain desired characteristics of the parental varieties and provides a marked improvement in the progeny. I have found that my new variety maintains its distinguishing characteristics by asexual propagation in quantity production by division of rhizomes as performed by me at my nursery in Salem, Oregon. It propagates easily and at a good rate of reproduction.

The distinctive features of this new variety are its prolific production of giant blooms of extraordinary substance, and which are larger than any tall bearded Iris plant in commerce, its predominantly rose coloring which is different from any other Iris variety, its vigorous growth, its pronounced candelabrum branching resulting in the complete freedom from crowding of its giant blooms, and the firm substance and the long-lasting qualities of its flowers.

This new variety of Iris plant is attractively formed with very broad arching or domed upper petals or standards and with massive, semi-flaring falls. The standards are distinctly crinkled at the extreme edges of the petals for about three-eights of an inch, but there is only a hint of crinkling at the tips of the falls. The heavy substance of the petals enables them to withstand heat, wind, and rain to an unusual degree and results in a freedom from floppiness that is unusual in Iris that even approach this one in size. The standards have a shimmering texture like taffeta silk, while the falls have a lacquered sheen.

These and other distinguishing characteristics of my new Iris plant variety are illustrated in the accompanying drawing in which.

Figure 1:
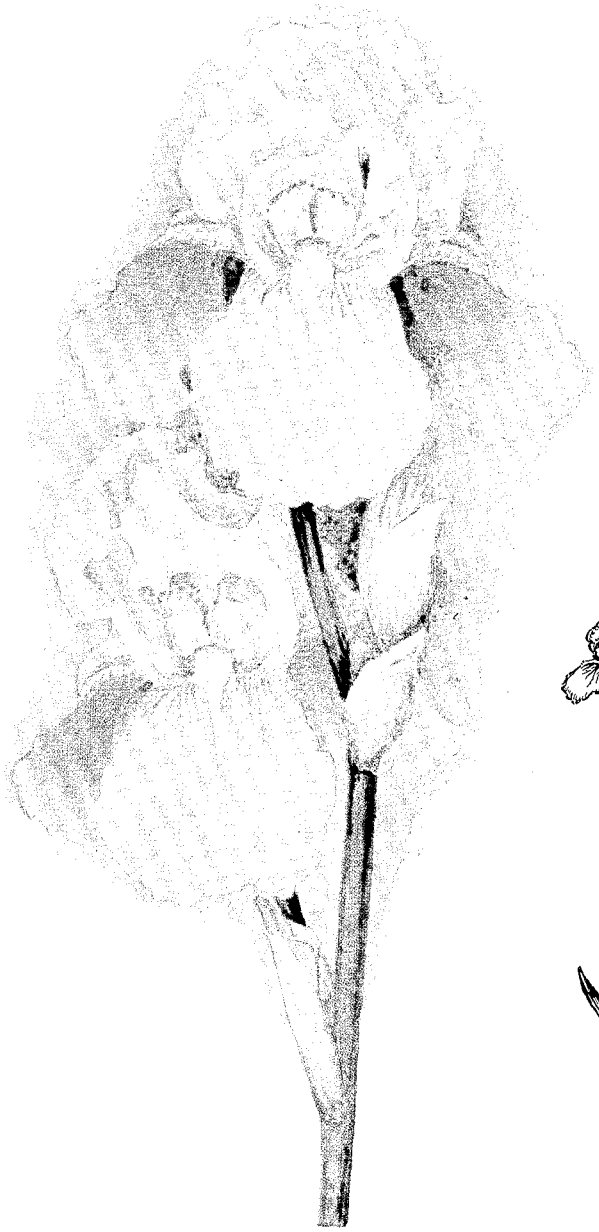
FIGURE 1 shows, in approximately true colors, a stem with two open flowers and two buds of the new variety.
Figure 2:
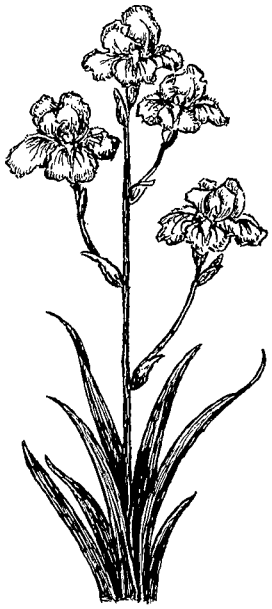
FIG. 2 is a pen and ink drawing illustrating the stalk and candelabrum branching.

In the detailed description which follows color plate references indicate Ridgeway's Color Standards and Nomenclature, while other colors refer to the ordinary dictionary meaning of the terms.

*Plant*

Growth: Vigorous.

Form: Mound form.

Stems: Approximately deep dull Yellow Green (No. 2) (Plate XXXII). Strong and heavy, rising to a height of 42 inches. Candelabrum side branches range from 11 inches on the lower part of the stem to 7 inches on the upper part of the stem.

Foliage: With—approximately 2½ inches, rising in mound form, and substantially 28 inches in height.

Color: Medium glaucous green typical of most tall bearded Iris; specifically French Green (Plate XXXII).

*Flower*

Bud:

*Size.*—Approximately 1½ inches long when color first shows, expanding rapidly to 4½ inches in length the day before unfolding into flower.

*Opening.*—Grows slowly until color shows, whereupon it develops rapidly.

*Color.*—Vinaceous Purple (Plate XXXVIII) at tip when bud first shows color, lightening to Eupatorium Purple (Plate XXXVIII) immediately before unfolding into flower.

*Spathe.*—Light green, the papery portion being Pale Chalcedony Yellow (Plate XVII).

Bloom:

*Size.*—11 to 11½ inches from top to bottom and approximately 8½ inches from side to side.

*Form.*—Classical, oval, with semi-flaring falls.

*Keeping qualities.*—Each flower lasts approximately 3 days and a single stem with its side branches will remain in bloom for 2–3 weeks.

*Blooming habit.*—Each stem with its side branches bears 10 to 11 buds and blooms.

*Color.*—Standards are predominantly Light Purplish Vinaceous (Plate XXXIX). Falls are halfway between Tourmaline Pink (Plate XXXVIII) and Persian Lilac (Plate XXXVIII). A narrow edging of ferruginous appears at the edges of the haft near the center of the flower. There is a moderate amount of venation across the haft, off-white alternating with Vinaceous Fawn (Plate XL). The beard is Apricot Yellow (Plate IV).

*Fragrance.*—Mild.

*Form of petals.*—Standards are cupped or domed, falls semi-flaring. Standards are crinkled at the edges for a width of about ⅜ inch. Only a trace of this crinkling appears at the tip of the falls.

*Size of petals.*—Both standards and falls are approximately 5½ inches from claw to tip and approximately 4½ inches wide.

Genital organs:

*Pistil.*—Style arms, 3; same color as standards.

*Stamens.*—Filaments, 3; 1⅝ inches long. Anther approximately ½ inch long. Color light yellow.

*Pollen.*—Copious quantity of pollen. Color creamy white. High fertility.

The two varieties of Iris plant which most nearly approach my new variety in appearance are "Lavanesque" (unpatented) and "Opal Beauty" (unpatented) and the principal differences are as follows:

My new variety of Iris plant is 50% larger than either "Lavanesque" or "Opal Beauty," both of which are under 7 inches in diameter.

My new variety is warmer and pinker in color than "Lavanesque," which is an orchid or lavender-pink rather than a rose-pink. My new variety is nearly a self-color, whereas "Lavanesque" is distinctly a bicolor with standards lighter than the falls.

My new variety is a more intense rose color than the pale silvery rose-pink of "Opal Beauty."

My new variety has distinctly crinkled edges on the standards unlike either "Opal Beauty," which is very plain petalled, or "Lavanesque," which is lightly waved or ruffled on the edges of both standards and falls.

Having thus disclosed my invention, I claim:

A new and distinct variety of Iris plant, substantially as herein shown and described, characterized particularly by the distinctly sparkling sheen of soft rose pink coloring of the flowers which are exceptionally large in size and having petals of heavy substance that precludes floppiness and resists the elements; very broad domed standards and massive semi-flaring falls; of unusual height, pronounced candelabrum stem-branching, broad foliage and ease of propagation.

No references cited.